United States Patent [19]
DeMarinis

[11] Patent Number: 4,652,642
[45] Date of Patent: Mar. 24, 1987

[54] AZIDOBENZAZEPINES

[75] Inventor: Robert M. DeMarinis, Ardmore, Pa.

[73] Assignee: SmithKline Beckman Corporation, Philadelphia, Pa.

[21] Appl. No.: 643,341

[22] Filed: Aug. 23, 1984

[51] Int. Cl.$^4$ ............................................. C07D 223/16
[52] U.S. Cl. .................................... 540/594; 436/815; 436/56; 436/57; 436/96
[58] Field of Search .................. 260/239 BB; 540/594

[56] References Cited
PUBLICATIONS

J. W. Regan et al., Proc. Natl. Acad. Sci., USA, 79, 7223 (1982).

Primary Examiner—Glennon H. Hollrah
Assistant Examiner—D. B. Springer
Attorney, Agent, or Firm—Joseph A. Marlino; Stuart R. Suter; Alan D. Lourie

[57] ABSTRACT

9-Azido-6-halo-3-lower alkyl-2,3,4,5-tetrahydro-1H-3-benzazepines are prepared from their 9-amino congeners. The compounds are useful as photoaffinity probes for $\alpha_2$-adrenoceptor sites in biological samples.

5 Claims, No Drawings

AZIDOBENZAZEPINES

This invention comprises 9-azido-6-halo-3-lower alkyl-2,3,4,5-tetrahydro-1H-3-benzazepines which are $\alpha_2$-antagonists and which have particular utility as novel photoaffinity probes for the $\alpha_2$-adrenoceptor in biological materials.

BACKGROUND OF THE INVENTION

My earlier filed U.S. patent application, Ser. No. 403,229, filed July 29, 1982, now U.S. Pat. No. 4,469,634, describes a series of allyloxytetrahydrobenzazepines which are of utility as immobilized ligands in affinity chromatographic columns for concentrating and purifying $\alpha_2$-adrenergic receptor containing biological matter. A corresponding scientific publication, J. W. Regan et al., Proc. Natl. Acad. Sci. USA 79 7223 (1982), describes this earlier work in greater detail.

The cited patent application also discloses the intermediate amino compounds related to the azides of the present invention.

To the best of my knowledge, the compounds described herein are the first azido-2,3,4,5-tetrahydro-1H-3-benzazepines to be prepared.

DESCRIPTION OF THE INVENTION

The compounds of this invention are represented by the structural formula:

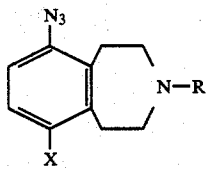

I in which:

X is halo such as chloro, bromo, fluoro or iodo; and, R is lower alkyl of 1-6 carbons.

The preferred species of formula I is 9-azido-6-chloro-3-methyl-2,3,4,5-tetrahydro-1H-3-benzazepine and its acid addition salts.

Also included in this invention are the pharmaceutically acceptable, acid addition salts of the above-described compounds with nontoxic acids, such as hydrochloric, sulfuric, sulfamic, acetic, propionic, nitric, hydrobromic, hydriodic, maleic, malic, methanesulfonic, ethanedisulfonic, p-toluenesulfonic or phosphoric acid salts. The salts are prepared by reacting the bases of this invention in an organic solvent with an excess of the chosen acid.

The compounds of this invention have antihypertensive activity with their mechanism of action being adrenergic alpha$_2$-antagonism.

This activity is demonstrated in vitro by determining the prejunctional alpha$_2$-antagonist activity using the isolated superfused guinea pig left atrium. Briefly, the heart is removed from a pentobarbital-anesthetized male guinea pig. The left atrium is removed, dissected free of extraneous tissue and mounted in a 2 ml superfusion chamber. The tissue is paced at 60 pulse/minute and the sympathetic nerves excited at 6 minute intervals by field stimulation. The response to nerve stimulation is measured as the difference in contractile force between the basal contraction and peak contraction following a nerve stimulation. A concentration-response curve for clonidine (a known alpha$_2$-agonist) is prepared by administering increasing concentrations of clonidine following each successive stimulation. The tissue is, then, superfused with the alpha$_2$-antagonist to be tested for thirty minutes and the clonidine concentration-effect curve is repeated in the presence of antagonist. The receptor dissociation constant of the antagonist ($K_B$) is defined as the antagonist concentration required to shift the log concentration-response curve of the agonist to the right by a factor of 2.

Details of the test system used to demonstrate alpha$_2$-antagonist activity, as well as activity of the standard antihypertensive compound, clonidine, are given in J. P. Hieble and R. G. Pendleton, Arch. Pharmacol. 309 217-224 (1979). The preferred species of this invention, i.e. the 9-azido-3-methyl-6-chloro compound, has a $K_B$ value of 158 nM in the atrium test.

The compounds of formula I have a unique utility as photoaffinity probes for the $\alpha_2$-receptor sites to specifically and irreversibly label the receptor. As such, they are of interest in biological research.

For example, the 9-azido-3-methyl-6-chloro compound has been demonstrated to bind competitively to $\alpha_2$ sites (Ki=42 nM) but, when irradiated with ultraviolet light, the binding effect is made irreversible. The photolytic inactivation is concentration and time dependent.

The concomitant presence of phentolamine, a nonselective adrenoceptor antagonist partially blocks the photolytic deactivation. Prazosin, an $\alpha_1$-selective antagonist, had no effect but p-aminoclonidine, an $\alpha_2$-selective agent, gave complete protection. This biological spectrum demonstrates the specificity of the compounds of this invention.

The photolytic effect is due to the chemical lability of the azido group to irradiation.

The compounds of this invention are prepared from the corresponding known 9-amino congeners by forming the diazonium ion at position 9 using sodium nitrite, acid and water at room temperature until the diazotization is complete. Then, sodium azide is added to complete the modified Sandmeyer reaction. The desired 9-azido compounds of formula I are isolated in good yield by standard chemical methods.

The following examples are to illustrate the preparation of the compounds of this invention. All temperatures are in degrees Centigrade. In the symbols used for halo atoms, radioisotopic forms commonly known in the art are included. For example, $I^{125}$ is an isotopic form often used in biological research.

EXAMPLE 1

To a cold solution of 67.2 g (0.34 mol, U.S. Pat. No. 4,265,890) of 6-chloro-3-methyl-2,3,4,5-tetrahydro-1H-3-benzazepine in 100 ml of sulfuric acid was added, dropwise over 2 hours, 40 ml of concentrated nitric acid. The mixture was stirred at room temperature overnight and quenched in ice. It was made basic with 10% sodium hydroxide solution and extracted with methylene chloride. The organic phase was washed, dried and evaporated to leave a residue, which was chromatographed over a "Waters prep 500" high pressure liquid chromatographic silica gel column, using isopropanol-hexanediethylamine, to give pure 6-chloro-3-methyl-9-nitro-2,3,4,5-tetrahydro-1H-3-benzazepine.

A solution of 10 g (0.04 mol) of the nitro compound and 6.0 ml of hydrazine hydrate in 400 ml of ethanol was warmed to 45° while activated Raney nickel was added in small portions until the evolution of gas ceased. The mixture was cooled, filtered through a filter aid and concentrated to give 9-amino-6-chloro-3-methyl-2,3,4,5-tetrahydro-1H-3-benzazepine.

To a solution of 630 mg (3 mmol) of 9-amino-6-chloro-3-methyl-2,3,4,5-tetrahydro-1H-3-benzazepine in 2 ml of concentrated sulfuric acid and 10 ml of water was added 280 mg (4 mmol) of sodium nitrate in 5 ml of water. The mixture was stirred in an ice bath during addition, then, allowed to warm to room temperature. After stirring at room temperature for one hour, 60 mg of urea was added to destroy excess nitrous acid. To this solution was added 330 mg (5 mmol) of sodium azide and the resulting solution stirred at room temperature. Nitrogen was evolved and a white precipitate formed. After stirring overnight, this was removed by filtration, stirred with a small amount of cold ethanol, filtered again and washed with ether to leave 545 mg (58%) of slightly off-white crystals, 9-azido-6-chloro-3-methyl-2,3,4,5-tetrahydro-1H-3-benzazepine sulfate. This material was crystallized from ethanol to give 390 mg as a slightly yellow crystalline solid, m.p. 71°–75° (dec), IR and NMR spectra support structure.

Anal. Calc'd for $C_{11}H_{13}N_4Cl.H_2SO_4.\frac{1}{4} H_2O$: C, 38.94; H, 4.72; N, 16.51. Found: C, 38.85; H, 4.40; N, 16.58.

An aliquot (100 mg) of the sulfate is shaken in ether with bicarbonate solution. The dried ether extract is evaporated to give the base. Half the base in ethanolic hydrogen chloride gives the hydrochloride salt. The remaining base in ethanol was reacted with an excess of methanesulfonic acid. Addition of ether and concentration gives the methanesulfonate salt.

Substituting a stoichiometric quantity of 6-fluoro-3-methyl-2,3,4,5-tetrahydro-1H-3-benzazepine or 6-bromo-3-butyl-2,3,4,5-tetrahydro-1H-3-benzazepine for the 6-chloro congener in the above sequence of reactions gives 9-azido-6-fluoro-3-methyl-2,3,4,5-tetrahydro-1H-3-benzazepine and its hydrochloride salt or 9-azido-6-bromo-3-butyl-2,3,4,5-tetrahydro-1H-3-benzazepine and its hydrochloride salt.

What is claimed is:

1. A compound of the structural formula:

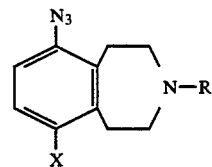

in which: X is chloro, bromo, or fluoro; and R is alkyl of 1–4 straight chain carbons, or a pharmaceutically acceptable acid addition salt thereof.

2. The compound of claim 1 being 9-azido-6-chloro-3-methyl-2,3,4,5-tetrahydro-1H-3-benzazepine.

3. The compound of claim 1 being 9-azido-6-chloro-3-methyl-2,3,4,5-tetrahydro-1H-3-benzazepine sulfate.

4. The compound of claim 1 being 9-azido-6-fluoro-3-methyl-2,3,4,5-tetrahydro-1H-3-benzazepine.

5. The compound of claim 1 being 9-azido-6-bromo-3-butyl-2,3,4,5-tetrahydro-1H-3-benzazepine.

* * * * *